(12) United States Patent
Joshi

(10) Patent No.: US 7,047,069 B2
(45) Date of Patent: May 16, 2006

(54) IONTOPHORETIC FLUID DELIVERY DEVICE

(75) Inventor: Ashok V. Joshi, Salt Lake City, UT (US)

(73) Assignee: Ceramatec, Inc., Salt Lake City, UT (US)

( * ) Notice: Subject to any disclaimer, the term of this patent is extended or adjusted under 35 U.S.C. 154(b) by 389 days.

(21) Appl. No.: 10/067,623

(22) Filed: Feb. 4, 2002

(65) Prior Publication Data

US 2003/0149393 A1 Aug. 7, 2003

(51) Int. Cl.
- *A61N 1/30* (2006.01)
- *A61N 1/00* (2006.01)
- *A61M 31/00* (2006.01)

(52) U.S. Cl. .......... 604/20; 604/501; 607/115

(58) Field of Classification Search ........ 604/20, 604/501; 424/442–449
See application file for complete search history.

(56) References Cited

U.S. PATENT DOCUMENTS

| | | | |
|---|---|---|---|
| 3,604,417 A | 9/1971 | Stolzenberg et al. | |
| 3,760,805 A | 9/1973 | Higuchi | |
| 3,760,984 A | 9/1973 | Theeuwes | |
| 3,797,494 A | 3/1974 | Zaffaroni | |
| 3,995,631 A | 12/1976 | Higuchi et al. | |
| 4,003,379 A | 1/1977 | Ellinwood, Jr. | |
| 4,034,756 A | 7/1977 | Higuchi et al. | |
| 4,140,122 A | 2/1979 | Kühl et al. | |
| 4,141,359 A | 2/1979 | Jacobsen et al. | |
| 4,240,884 A | 12/1980 | Pellegri | |
| 4,292,968 A * | 10/1981 | Ellis | 604/20 |
| 4,452,249 A | 6/1984 | Sachs et al. | |
| 4,522,698 A | 6/1985 | Maget | |
| 4,539,004 A | 9/1985 | Eckenhoff et al. | |
| 4,886,514 A | 12/1989 | Maget | |
| 4,929,233 A | 5/1990 | Roth et al. | |
| 5,035,711 A | 7/1991 | Aoki et al. | |
| 5,041,107 A | 8/1991 | Heil, Jr. | |
| 5,063,175 A | 11/1991 | Broadbent | |

(Continued)

FOREIGN PATENT DOCUMENTS

EP     0 931 564 A1     7/1999

OTHER PUBLICATIONS

PCT International Search Report, PCT/US09/03282, dated Jul. 31, 2003, 5 pages.

Scott et al. electrochemically reactive cathodes for electrotransport device, US Patent Pub No. US 2002/0055704.

*Primary Examiner*—Brian L. Casler
*Assistant Examiner*—Roz Maiorino
(74) *Attorney, Agent, or Firm*—TraskBritt

(57) ABSTRACT

A low cost, accurate, single use, disposable, iontophoretic fluid delivery device having cationic and anionic chambers separated by container structure and arranged to promote a flow of treatment ions into a body. The device desirably uses rugged minibatteries safely to provide increased electromotive force to the ion transfer process compared to galvanic cells having electrolyte matched to a human body's electrolyte. Minibatteries may be located in one or both cationic and anionic chambers, and/or attached to structure of a container outside the chambers. A shunt resistance may be arranged in a parallel circuit to the body to control delivery of a beneficial agent in any amount between 1 mAmp-min to 500 mAmp-min, or more. Substrates, located in the chambers and adapted to hold electrolyte or treatment drugs, may be electrically conductive to resist polarization of the chemicals near a conducting terminal. Cationic and anionic chambers may be made having different sizes and/or shapes to facilitate placement of treatment drugs into the correct chamber.

5 Claims, 5 Drawing Sheets

U.S. PATENT DOCUMENTS

| | | |
|---|---|---|
| 5,250,023 A | 10/1993 | Lee et al. |
| 5,286,254 A | 2/1994 | Shapland et al. |
| 5,413,572 A | 5/1995 | Wong et al. |
| 5,427,870 A | 6/1995 | Joshi et al. |
| 5,454,922 A | 10/1995 | Joshi et al. |
| 5,492,534 A | 2/1996 | Athayde et al. |
| 5,618,265 A | 4/1997 | Myers et al. |
| 5,672,167 A | 9/1997 | Athayde et al. |
| 5,700,481 A | 12/1997 | Iga et al. |
| 5,735,897 A | 4/1998 | Buirge |
| 5,869,078 A | 2/1999 | Baudino |
| 5,876,741 A | 3/1999 | Ron |
| 5,911,223 A | 6/1999 | Weaver et al. |
| 5,954,268 A | 9/1999 | Joshi et al. |
| 5,971,722 A | 10/1999 | Maget et al. |
| 5,983,130 A * | 11/1999 | Phipps et al. .............. 604/20 |
| 6,261,595 B1 | 7/2001 | Stanley et al. |
| 6,421,561 B1 * | 7/2002 | Morris ...................... 604/20 |

\* cited by examiner

IONTOPHORETIC FLUID DELIVERY DEVICE

TECHNICAL FIELD

The present invention relates to apparatus and methods for delivering drugs or other beneficial agents. More specifically, the present invention relates to iontophoretic electrotransport devices and methods of their use in delivering treatment to a body.

BACKGROUND

Iontophoretic transport of drug or biological treatments is well known and is commonly used as one way to transport such treatments across a surface and into a body. Many iontophoretic devices have been developed, as witnessed by the quantity of issued patents and pending applications mentioning such phenomena. A representative such application, titled "Rate Adjustable Drug Delivery System" filed by Birch Point Medical, Inc., was published Jul. 12, 2001 as international publication No. WO 01/49365 A1. The '49365 application is hereby incorporated by this reference as though set forth in full herein.

Existing iontophoretic devices may generally be classified into two groups based upon their electromotive source. The first such group may be characterized as disposable and is driven by a galvanic or electrochemical reaction encompassing electrodes bathed in an electrolyte carrying the treatment ions and offering a relatively low voltage. Such devices inherently require long treatment time intervals. Such devices are also generally constructed to be inexpensive, used once, and then thrown away. The second type of iontophoretic device typically is driven by an auxiliary power module. While treatment time requirements for devices having auxiliary power modules are generally reduced, the power modules are expensive and so typically must be reused.

A representative disposable device, generally indicated at 30 in FIG. 1, can be constructed on an adhesive strip 33. Cationic chamber 35 and anionic chamber 37 are formed in the adhesive strip 33 to create separated volumes in which to house cationic and anionic treatment materials, respectively. An electrolytic cell created by a chemical reaction between the cationic and anionic electrodes in an electrolyte provides the electromotive force to operate the device for ion transfer to a patient. A first electrode 39 installed in the cationic chamber 35 and a second electrode 41 installed in the anionic chamber 37 are connected by a conductor 43 to form an electron-transporting leg of an electric circuit. Application of the adhesive strip to a human body completes the circuit and initiates a flow of treatment ions through the patient's skin.

An electrode 39 may be formed from zinc, with an electrode 41 being made from silver chloride. The electrolyte contained in the cationic chamber 35 and anionic chamber 37 directly contacts the skin to be treated and necessarily is limited in reactivity to avoid skin irritation. Conductive salt solutions (such as 1% NaCl) commonly are employed as electrolytes due to their compatibility with a patient's skin. A device 30, as described, will generate an electromotive force for ion transfer totaling about 1 Volt. In use of a device 30, there is some possibility that a desired treatment chemical may undesirably interact with the electrolyte, electrode, or a product of the galvanic reaction, thereby compromising a treatment.

An alternative construction of a disposable-type device is generally indicated at 50 in FIG. 2. As a way to increase the voltage between the cationic chamber 35 and anionic chamber 37, a plurality of galvanic cells may be arranged in electrical series on an adhesive strip 33. Two such cells are illustrated in the embodiment 50. A first electrode 39 in the cationic chamber 35 is connected in series by a conductor 43 to electrode 53 in cell 55. Electrode 57, also housed in cell 55, is then connected in series by a conductor 43 to electrode 41 in cationic chamber 37. Such a two-cell arrangement can effectively double the voltage generated by the device and can therefore reduce a length of treatment time required. Additional cells may be added in series; however, the adhesive strip 33 rapidly becomes crowded, thereby limiting the practical range in electromotive force for a device 30.

FIG. 3 illustrates an exploded cross-section view through a device 30. As illustrated, the cationic chamber 35 and anionic chamber 37 typically are open toward the patient. Some sort of substrate 59 typically is provided as a receptor to hold the treatment chemicals (beneficial agent) or electrolyte in a chamber prior to installation of adhesive strip 33 onto a patient. Substrates 59 typically are made from gauze, cellulose, cotton, or other hydrophilic material. It is common practice to saturate the substrates 59 just prior to attaching an adhesive strip 33 to a patient for a treatment session. Substrates 59 may be loaded with treatment substances using a syringe or any other convenient transfer implement.

A representative device driven by a reusable auxiliary power module is illustrated generally at 60 in FIG. 4. A power module 63 typically houses sophisticated electronics and is relatively expensive (power modules are generally not regarded as single-use, disposable items). Power module 63 may provide a substantial voltage to cause ion migration through a body. Applied voltages may reach perhaps 90 Volts, although perhaps for only a very short period of time to initiate ion transfer. Depending upon the skin contact area for ion transfer from a treatment chamber and the composition of the beneficial agent, a patient may perceive a burning sensation under an applied voltage of only 30 volts. Power modules may be attached directly to an adhesive strip 33, as illustrated, but are more commonly connected in-circuit between the cationic chamber 35 and anionic chamber 37 using wires, or extension leads 65, to permit some degree of motion for a patient undergoing a treatment.

The electronics portion of a power module 63 may be constructed to generate a range of voltages, hold a voltage substantially constant for a period of time, or cause a programmable range in voltage over a period of time. Similar modulation may be made by a power module 63 to a current flowing in the circuit. However, power modules 63 represent an expense and may cause inconvenience in that operators may require special expertise to properly configure the module for a particular treatment.

A patient would benefit from a simple, disposable, iontophoretic device capable of higher voltage and more sustained current transmission than commercially available disposable devices, but being less costly than devices requiring an electronic module. An improvement in current transmission to minimize a polarization effect in commercially available disposable devices would also be an advance. A disposable iontophoretic device having a treatment time operably controlled by the working life of a disposable power source having a square-wave current flow would be an additional advance.

SUMMARY OF THE INVENTION

The invention provides an apparatus and method for delivering a treatment to a body by way of an iontophoretic transport procedure. A device constructed according to principles of the instant invention provides a low-cost, disposable, single-use, fast and accurate, iontophoretic fluid delivery device for external or implantable use. A body may be construed specifically as a mammalian (e.g., human or animal) body or, alternatively and generally, as a container of an electrolyte. A treatment to be applied to a body by the instant device and method may be either cationic-based or anionic-based.

An iontophoretic fluid delivery device within contemplation typically includes a cationic chamber, an anionic chamber, and an electromotive force to promote ion exchange between a body and one or both of the chambers. The cationic and anionic chambers define separate volumes in which are held cationic and anionic substances, respectively. A wall of each chamber provides a passageway, or opening, through which ions may migrate. The passageways are generally oriented and arranged on a surface of a container to enable creation of a first conductive path, through a cooperating body, of an electrical circuit between the cationic and anionic chambers.

Treatment materials may be loaded, by syringe or other transfer mechanism, onto a substrate housed within a chamber. Substrates desirably may be configured to reduce polarization of the treatment materials with an attendant drop in reaction rate. One such configuration includes an electrically conductive substrate affixed to a wall of one of the chambers. A workable such substrate may have a surface area, for electron transfer, sized substantially in correspondence with an opening of an ion transfer passageway. An alternate substrate may be formed as an electrically conductive gauze. The conductive gauze may be dispersed substantially throughout the volume of the chamber. A hydrogel substance operable as an electrolyte can be disposed, substantially as a preloaded item, in one or both of the cationic or anionic chambers. Such a preloaded hydrogel can reduce preparation time of a treatment by requiring only the treatment to be introduced, and only to a single chamber of the container.

Devices operable primarily as anionic treatment devices may be made to have a color, texture, shape, or size to differentiate them from a cationic treatment device. Furthermore, individual chambers housed by a container may be made to have different sizes or shapes to facilitate identification and loading of treatment materials into the correct chamber.

One exemplary container can be embodied as an adhesive strip or patch. Alternatively, the container may be a cartridge, carton, or tube for insertion into a body. Devices adapted for insertion into a body, or adapted for storage in preloaded form, may include semipermeable membranes disposed as passageway coverings to contain treatment substances within separate chambers prior to use of a container during a therapeutic treatment.

The electromotive force required to operate the device desirably is supplied by an electromotive cell (such as a self-contained minibattery), located in a second electrically conductive path configured to complete the electrical circuit between the cationic and anionic chambers. Preferred cells will have an approximately square-wave current discharge over their working life. Serviceable electromotive cells may be constructed containing electrochemically reactive matter in an amount operable to control a length in time of the cell's working life. Furthermore, the operable or working life of the electromotive cell desirably is set to be in harmony with the desired treatment time and can, therefore, be used as a measurement control to resist overtreating of a patient. The working life of the battery may be determined or manipulated by circuit elements such as a shunting resistor in a circuit parallel to an ion-conducting path. Electromotive cells within contemplation nonexclusively include minibatteries constructed to operate with a metal-anode-based electrochemical reaction using lithium, zinc, magnesium, or aluminum. Such self-contained minibatteries can be made rugged to withstand incidental abuse without incurring sufficient damage to suffer a leak of their contents. Such batteries may also be made in a thin and flexible form to reduce container bulk.

Certain preferred iontophoretic devices may use one or more electromotive cells, as required, e.g., to control a length of time for, or rate of, delivery of a quantity of a treatment ion to a body. Such cells may be located partially or completely inside either one or both chambers, or attached to the container in some convenient location. In addition to providing treatment control through their inherent operating life, cells may be arranged in series to provide an increased voltage over a single cell. The increased voltage may permit a reduction in a time of treatment application.

A cell located partially, or totally, within a chamber generally includes a fluid-resistant barrier to isolate an electrolytic path between the cell's positive and negative poles. In such case, a portion of either a positive or a negative pole may be exposed for electron transfer directly to an electrolyte. The cell housing may optionally be formed from, or coated with, a noble or inert metal to avoid its undergoing an undesirable chemical reaction with treatment chemicals. Alternatively, an inert metal may be placed, as an electron interface for the electrochemical reaction, in-circuit between an exterior cell and interior treatment chemicals.

One embodiment of the instant invention includes a first electromotive cell disposed interior to the cationic chamber. The first cell has an electrolyte barrier exposing only a portion of its negative pole. A second cell, in electrical series with the first cell, may be included interior to the anionic chamber. The second cell also has an electrolyte barrier, but exposing a portion of its positive pole. A conductive path between the two cells is generally sealed to resist transmission of electrolyte from or between the chambers. The invention may alternatively include a single electromotive cell, located in either of the chambers, as desired and practical. In another arrangement, the single electromotive cell may be affixed to a container structure separate from both chambers. An embodiment may have electromotive cells located in each chamber, with one or more additional cells located exterior to the chambers and attached to structure of the container. An arrangement of subcells adjacently stacked in electrical series may be regarded as a single electromotive cell for the purpose of packaging in a chamber, or on a container.

Additional circuit components may be included in the second conductive path to increase treatment options and efficacy. As a non-limiting example, an oscillator element can be disposed in-circuit in the second conductive path and operate to control a current flow between high and low values. A switch placed in the second path may be used to start and stop treatments at controlled intervals.

One method of using the instant device, for iontophoretic treatment of a patient, includes the steps of: a) providing an iontophoretic fluid delivery device having a cationic chamber and an anionic chamber, one of the chambers containing a hydrogel; b) adding a fluid only to one of the chambers to form an electrolyte treatment; and c) affixing the device to a surface of a patient's body for a duration of time as required to transfer a desired quantity of treatment to the patient.

These features, advantages, and alternative aspects of the present invention will be apparent to those skilled in the art from a consideration of the following detailed description taken in combination with the accompanying drawings.

BRIEF DESCRIPTION OF THE SEVERAL VIEWS OF THE DRAWINGS

In the drawings, which illustrate what are currently considered to be the best modes for carrying out the invention.

DETAILED DESCRIPTION OF THE INVENTION

Reference will now be made to the drawings in which the various elements of the invention will be given numerical designations and in which the invention will be discussed so as to enable one skilled in the art to make and use the invention. It is to be understood that the following description is only exemplary of the principles of the present invention and should not be viewed as narrowing the claims which follow.

Figure 1:
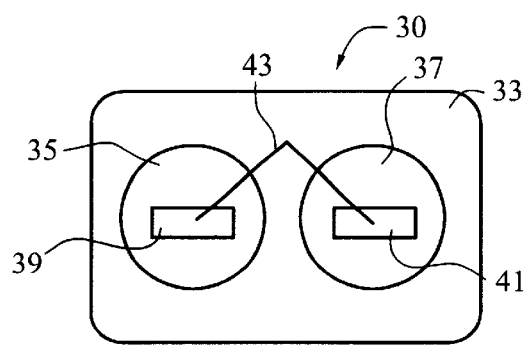
FIG. 1 is a top view of a first prior art iontophoretic device.
Figure 2:
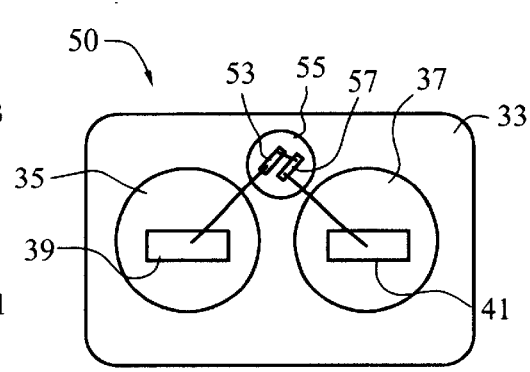
FIG. 2 is a top view of a second prior art iontophoretic device.
Figure 4:
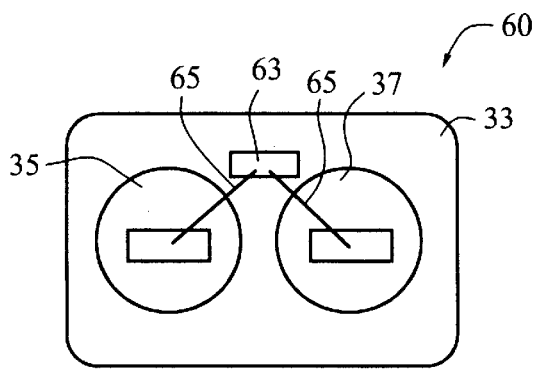
FIG. 4 is a top view of a third prior art iontophoretic device.
Figure 3:
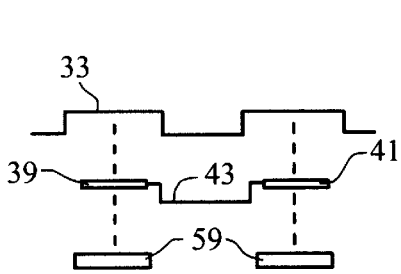
FIG. 3 is an exploded side view, in section, of the prior art device depicted in FIG. 1.
Figure 5:
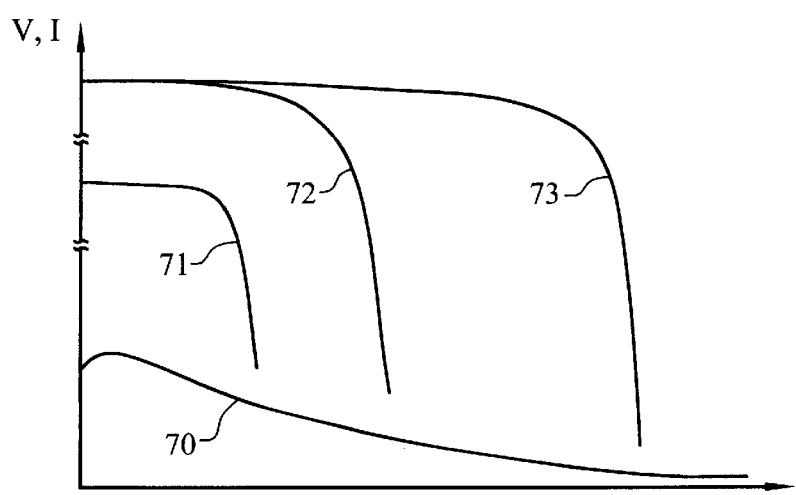
FIG. 5 illustrates current rate characteristics of certain iontophoretic devices.

A plot of current discharge or voltage verses time is presented in FIG. 5, with the horizontal axis indicating a time scale and the vertical axis showing either a current flow or available voltage. Trace line 70 is representative of a current profile obtainable in a commercially available and disposable galvanic cell device, such as device 30. Trace line 70 shows a reduced current flow over time due to polarization of electrolyte in the areas surrounding the electrodes and a corresponding reduced rate of chemical reaction. Trace lines 71–73 are achievable in minibatteries, with the current, or voltage, fall-off occurring when one, or both, reactant is substantially spent in the chemical reaction.

Traces 71–73 illustrate desired current profiles of electromotive cells, such as minibatteries, characterizable as having a substantially "square-wave" over their working life, assuming a sustainable (sufficiently slow) current flow. The working lifetime of such a minibattery may be controlled to have a desired length by providing only a measured amount of one or more reactant chemicals. The operational life of a minibattery may be set to last 20 seconds, 20 minutes, or multiple hours, simply by controlling the quantity of reactive components in the battery. For example, a battery with the characteristics indicated by trace line 73 may be assembled having about twice as much reactant compared to a battery with the characteristics indicated by trace line 72. A treatment interval may, therefore, conveniently be determined by the life of a battery. Of course, a treatment time may simply be established by operation by a patient, or by a health care practitioner, of a switch to start and stop a flow of current through the device. The total treatment dose may alternatively also be limited by loading a device with a controlled amount of the ion medicament.

As indicated by traces 71–73 in FIG. 5, a minibattery also may be constructed to produce a higher voltage than a typical disposable galvanic cell contained in a device 30. A desired voltage may be created by combining oxidizing and reducing agents having sufficient galvanic activity. A battery having the characteristics indicated by trace line 71 would have constituent components with lower combined reactivity than a battery having the characteristics indicated by trace lines 72 and 73. Batteries may also be arranged in electrical series to boost a voltage supplied by a composite cell, effectively forming a more powerful battery. Such a higher voltage may beneficially establish a flow of ions and cause the ions to migrate at an increased rate to reduce a treatment time requirement. A treatment interval may also be determined, in part, by the voltage of a battery, or effective battery.

Minibatteries may be manufactured having rugged housings to withstand incidental, or even significant, abuse without incurring sufficient damage to suffer a leak of their contents. For the purpose of this disclosure, a battery housing is understood to be rugged if the housing is capable of transferring tissue-damaging loads to a patient while avoiding a content-leaking rupture. A minibattery having a paper housing, for example, would be susceptible to developing a leak which could harm a patient.

A familiar example for a rugged minibattery type is a button-type battery, which is typically housed in a metal canister resembling a button. Such batteries are commonly employed as power sources for wrist watches. A patient wearing an iontophoretic device incorporating such type of rugged battery would be seriously injured before such a metal button battery would leak due to an object contacting the battery. The rugged housing permits safe use of more reactive materials, such as Lithium, Sodium Hydroxide, and Potassium Hydroxide, with correspondingly higher voltage battery outputs than galvanic reactions using low-concentration electrolyte matched to a human body. Minibatteries are low-cost devices and are available having voltages between about one (1) Volt and about fifteen (15) Volts. The increased voltage provided by a minibattery permits a reduced treatment time in a disposable, single-use, iontophoretic device. Rugged minibatteries may also be made in a thin and/or flexible form to reduce bulk of a treatment device. A desirable minibattery for use in the instant invention may be constructed to operate with various metal-anode-based electrochemical reactions. Such an anode metal may include Lithium, Zinc, Magnesium, and Aluminum.

Certain embodiments of the present invention differ from the prior art by providing an electromotive force, to drive ion migration, in a self-contained disposable package. A self-contained package may be regarded as providing an electromotive source having a positive pole and a negative pole defined within a single housing. Chemically reactive materials to create a voltage between the positive and negative poles are included inside that housing during manufacture of the electromotive source. The housing is sealed to enclose all of the reactive elements required for electron production. No additional materials, such as electrolyte, must be added subsequent to manufacture of the electromotive source before the source can be used in an electric circuit. Such package structure differentiates over structure of an electromotive source formed by galvanic coupling between a plurality of chambers, such as is found in commercially available and disposable iontophoretic devices. A suitable self-contained package to provide such electromotive force can be embodied as a minibattery, including button-cell type minibatteries. Such a minibattery may be the sole electromotive source, or may augment a conventionally distributed galvanic reaction arrangement, of a disposable iontophoretic device.

Figure 6:
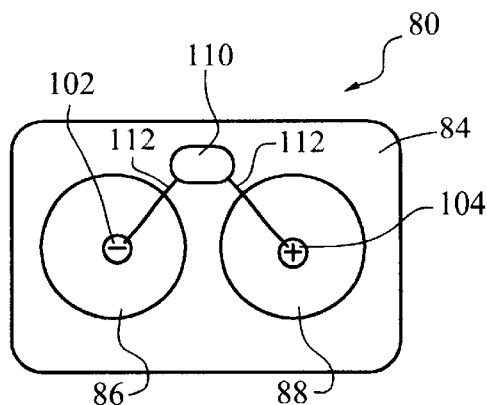
FIG. 6 is a top view of an iontophoretic device according to the instant invention.

One embodiment of the present invention is illustrated, generally at 80, in FIG. 6. A container 84 spaces apart a cationic chamber 86 and an anionic chamber 88. The chambers are spaced apart to enable creation, with a cooperating body, of an ion-conducting path of an electric circuit. The ion-conducting path portion of the electric circuit transports the treatment ions into the body.

The container 84 may be sized in correspondence with an area of a patient to be treated. For example, local cosmetic treatment of dark areas under a patient's eyes requires a container sized to attach to a small area. General treatment of a human body with drugs, such as lidocaine, may be better accomplished using the larger surface area available on a patient's shoulder, arm, or area of a torso. Containers 84 may advantageously be formed from a flat and flexible adhesive strip to conform and adhere to a body surface. Containers may also be made in the form of a cartridge, capsule, or tube for insertion into a body volume.

With continued reference to FIG. 6, a first electromotive cell 102 is located in the cationic chamber 86 of device 80. A second electromotive cell 104 is located in the anionic chamber 88. Cells 102 and 104 may be partially or completely inside the respective chambers. It is further within contemplation for a device according to the present invention to have a single minibattery, which may be located in either of chambers 86 or 88, or simply attached to a container 84. Optional circuit elements 110, nonexclusively including an oscillator, a switch, a resistor, a capacitor, and the like, may be present in certain embodiments. If present, such circuit elements 110 typically are located in an electronconducting path 112 (also referred to herein as "conductor 112") between the cationic chamber 86 and the anionic chamber 88.

A fluid barrier is created on each electromotive cell in illustrated embodiment 80 to prevent a circuit being formed by electrolyte in a chamber and carrying current between the individual cell's positive and negative poles. Such a current would detrimentally drain the cell and impede operation of a treatment device 80. One way to create a workable fluid barrier on a pair of minibatteries involves placing the batteries in a die. One battery is placed with its negative pole upwards, and the other battery is placed in the die having its positive pole upwards. The spacing between the batteries in the die should be sufficient to permit location of the batteries as desired in a container 84. A conductor 112 may be attached between both of the upwardly facing poles, or both of the downwardly facing poles, by spot welding, or using a conductive adhesive. A preferably inert fluid-sealing material, such as an epoxy, plastic, rubber, urethane, or a silicone-based product, is then applied to portions of the conductor and minibatteries to form the electrolyte barrier. The barrier-forming material may be painted on, sprayed on, or injected into the die. A portion of one pole of each battery is left uncovered by the electrolyte barrier so that one positive pole and one negative pole are exposed for connection in an electric circuit.

Figure 7:
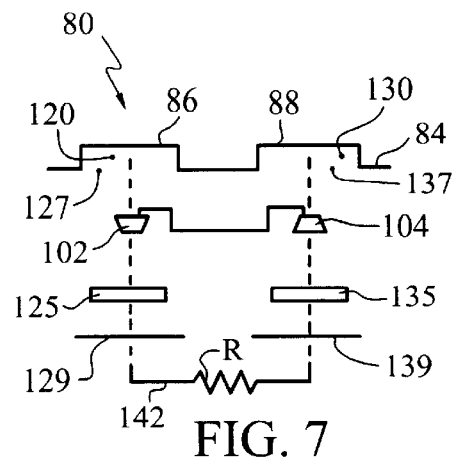
FIG. 7 is an exploded side view of the device illustrated in FIG. 6.

Additional details of construction of a representative device 80 are illustrated in FIG. 7. Structure of container 84 spaces apart cationic chamber 86 and anionic chamber 88. Cationic chamber 86 defines a volume 120 in which may be received a minibattery 102 (previously called "electromotive cell"), a portion of conductor 112, and a substrate 125. A passageway 127, formed through a wall of catanionic chamber 86, provides a path for ion migration toward or away from the catanionic chamber 86. In certain embodiments, an optional semiporous membrane covering 129 may be included to provide a retainer for treatment substances in the catanionic chamber 86. Such a covering 129 will be sufficiently permeable to permit ion migration, but desirably will resist fluid flow from the chamber. A chamber covering 129 may be used to enable preloading of medicament into a stored device, or in the case where a device is inserted into, or placed on, a body.

Still with reference to FIG. 7, anionic chamber 88 defines a volume 130 in which may be received a minibattery 104 (previously called "electromotive cell"), a portion of conductor 112, and a substrate 135. A passageway 137, formed through a wall of anionic chamber 88, provides a path for ion migration toward or away from the chamber 88. In certain embodiments, an optional semiporous membrane covering 139 may be included to provide a retainer for treatment fluids, such as drugs, in the chamber 88, while permitting ion migration through the passageway 137. A device 80 may be attached to a surface of a cooperating body to complete an electric circuit through the body, represented by conductor 142 and resistor R. For the purpose of this disclosure, a cooperating body is intended to encompass any structure capable of completing an electric circuit by forming a physical contact spanning between the passageways 127 and 137 to form an ion-transporting leg of the circuit. Serviceable bodies include human and animal bodies and other structures which may be considered, in a general sense, to act as containers of electrolyte.

The cationic chamber 86 and anionic chamber 88 typically are formed to define relatively wide and shallow volumes. Passageways 127 and 137 desirably are large to provide a correspondingly large contact area over which ions may migrate into a body. The chamber volumes 120, 130 are generally shallow to minimize a distance, in a depth direction, ions must travel before entering a body. However, polarization of the electrolyte near conducting terminals commonly occurs and is the source of current reduction depicted by trace 70 in FIG. 5. One way to decrease the polarization effect is to form substrates 125 and 135 to include conductive elements arranged to better distribute electrons through the chamber volume. In any case, a distributed current transmission is desirable in both types of iontophoretic devices. A desirable distribution may limit an effective sustained current density over a treatment area to less than about 0.5 mA/cm$^2$ to reduce the chance of a patient experiencing skin irritation during a treatment.

Substrates 125 and 135 may include conductive material affixed to a wall area of one or both chambers. Such conductive material may be painted, sprayed, or otherwise affixed to a portion of, or on the entire inside surface of, a chamber. Desirably, such conductive material will encompass an area opposite, and sized in agreement with, a passageway 127 or 137. Alternatively, a substrate 125 or 135 may be formed from a conductive material and distributed through a volume 120 or 130. A workable distributed substrate may be formed by impregnating a conventional substrate, such as a gauze, with a conductive substance, such as a metal powder. A substrate also may be made from a metal or metal/polymer composite.

Figure 8:
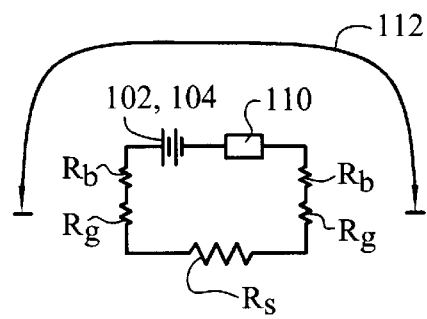
FIG. 8 is an electric schematic of an iontophoretic circuit.

FIG. 8 illustrates an electric schematic of an iontophoretic reaction process. Resistances to current flow in such a circuit include $R_b$, for resistance through the battery, $R_g$, for resistance through the gauze or from a terminal to an electrolyte, and $R_s$ representing skin resistance of a body. Polarization of the constituent chemicals in a conventional disposable galvanically driven iontophoretic reaction tends to increase a value for $R_g$, and decrease a transmitted current. Distributing a surface for electron transfer through a volume of a chamber tends to counter onset of such polarization. The benefit to a patient undergoing a treatment with improved electron distribution is an increased and consistent ion delivery rate, permitting a reduced treatment time interval.

It is desirable for conductors 112 and exposed portions of electromotive cells 102, 104 to not detrimentally react with treatment chemicals in a chamber 86 or 88. A detrimental reaction would decrease efficacy of the treatment, or may form a caustic or noxious substance which might irritate a patient's skin. One way to resist such undesired chemical interaction is to provide a minibattery or electromotive cell with an inert housing, or coating. An exposed electron exchange surface portion may be made from, or coated with, a chemically inert conductor or noble conductive material. For the purpose of this disclosure, a noble conductor can be defined as a material serviceable to conduct electrons, but otherwise generally nonparticipatory in a chemical reaction with substances in which it is immersed or contacting. Examples of such noble conductive materials non-exclusively include molybdenum, gold, silver, carbon, titanium, and tantalum. As an additional precaution, a battery may be located external to a chamber and electrically connected to a noble conductor located inside a chamber for electron exchange.

Figure 9:
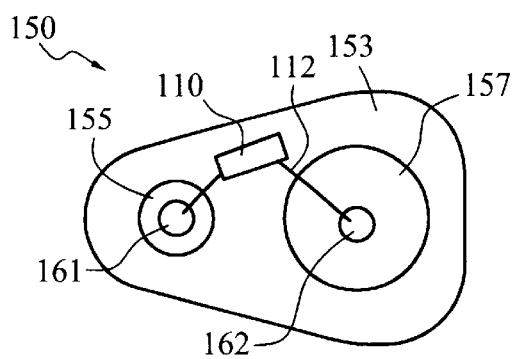
FIG. 9 is a top view of an alternative embodiment of the invention.

Iontophoretic devices according to the instant invention, such as indicated generally at 150 in FIG. 9, may be constructed having a different size or shape between cationic and anionic chambers. The shape, color, texture or some other discernable characteristic of container 153 may also be used as an indicator of the device's use for cationic or anionic treatments. For example, a red container 153 may signify that the device 150 is for use to dispense anionic-based treatments. A yellow container 153 may signify that the device 150 is adapted to dispense cationic-based treatments. For convenience, a chamber 155 may be preloaded for storage with a hydrogel capable of acting as an electrolyte. A treatment drug then need only be loaded into chamber 157 prior to placing the container 153 onto a body. The shape and/or size difference between chambers 155 and 157 can assist in loading the treatment into the correct chamber to establish treatment ion migration directed toward the body. Of course, an exposed, or electrolytically connectable, pole of each of batteries 161 and 162 will have an appropriate electrical sign, depending on the construction and desired purpose of the device 150 as either a cationic or anionic beneficial agent dispensing device.

Figure 10:
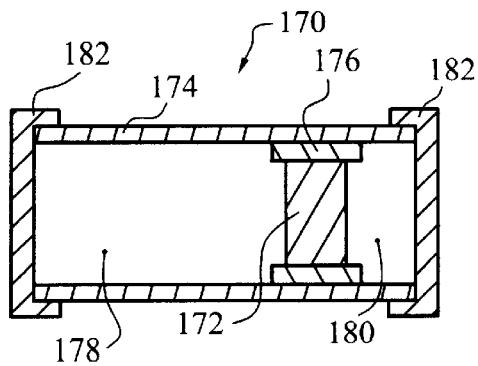
FIG. 10 is a plan view in section of an implantable embodiment of the invention.

One embodiment of an implantable iontophoretic device according to the instant invention is illustrated generally at 170 in FIG. 10. In one use, device 170 may be surgically implanted into a body to provide a long-term pain treatment. A device 170 has an electromotive source 172 housed in a container 174. Illustrated container 174 is constructed as a cylinder. A barrier 176, adapted to prevent an electrolytic circuit between positive and negative poles of electromotive source 172, is included when the electromotive source 172 includes one or more minibatteries. Barrier 176 may be adapted sealingly to slide like a piston inside container 174 to accommodate a change in chamber volume due to transfer of ions from a chamber containing a beneficial treatment agent. Alternatively, a container can be constructed directly to expand or contract and thereby accommodate changes in chamber volume. Chamber 178 can be a cationic chamber when chamber 180 is an anionic chamber. Of course, reversing the polarity arrangement of the electromotive source 172 will reverse each chamber's role. Some sort of semipermeable cap 182 is provided to cover openings from the respective chambers. Suitable caps 182 permit migration of ions in and out of the chambers, but otherwise resist unintended leaking of chamber contents.

Commercially available minibatteries typically provide a higher capacity, or contain more stored energy, than required to dispense a desired ion dose of a beneficial agent. A device according to the present invention may be adapted accurately to dispense a controlled dose of beneficial treatment by incorporating a suitable circuit arrangement in the electron-carrying portion of the device's electric circuit. An electric circuit may be arranged to direct virtually any portion of an electromotive source's available stored energy, from zero to 100 percent, to ion transport.

Figure 11:
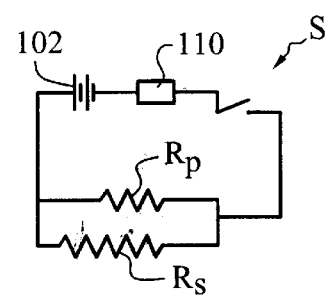
FIG. 11 is an electric schematic of an iontophoretic circuit.

One way to apportion a source's stored energy is illustrated in FIG. 11. A shunt resistor, $R_p$, can be connected in-circuit to form an electron-conducting path parallel to the ion-conducting path through a body. A representative switch S can conveniently be closed by loading a chamber with electrolyte and application of a device to a body to complete the circuit. As is well known in electric circuit design, the current flow through the shunt resistor $R_p$ and the body resistance $R_s$, will be determined by the relative magnitude of the resistance in each path. Decreasing the value for $R_p$ increases the current flow through the parallel path and decreases the current flow through the ion-conducting path, resulting in a lower dispensed beneficial agent ion dose. A device may, therefore, be constructed to deliver a dose of ion-based treatment corresponding to any portion of a battery's capacity.

Figure 12:
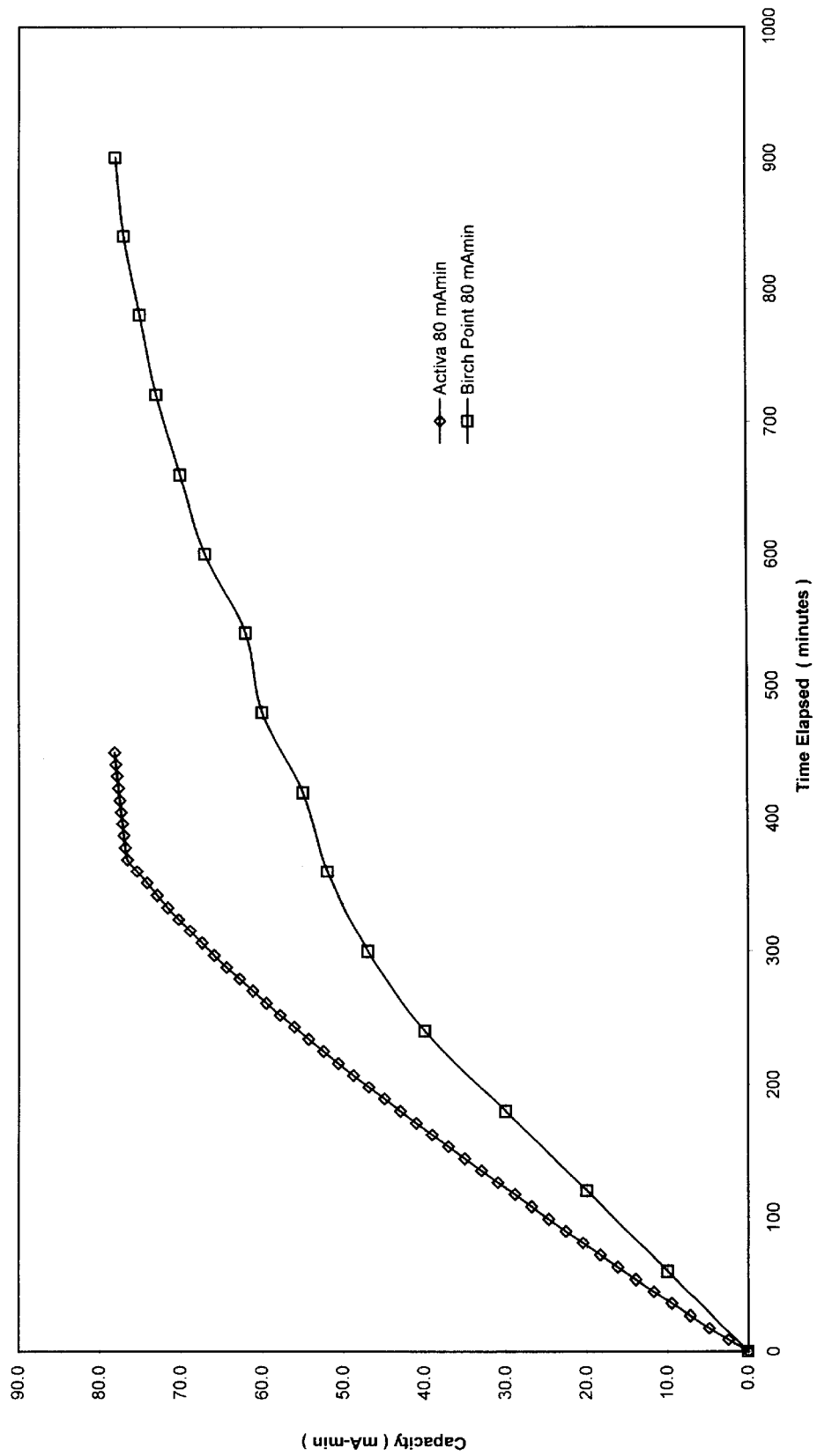
FIG. 12 is a plot illustrating cumulative delivery from a device constructed according to the invention compared to a prior art device.
Figure 13:
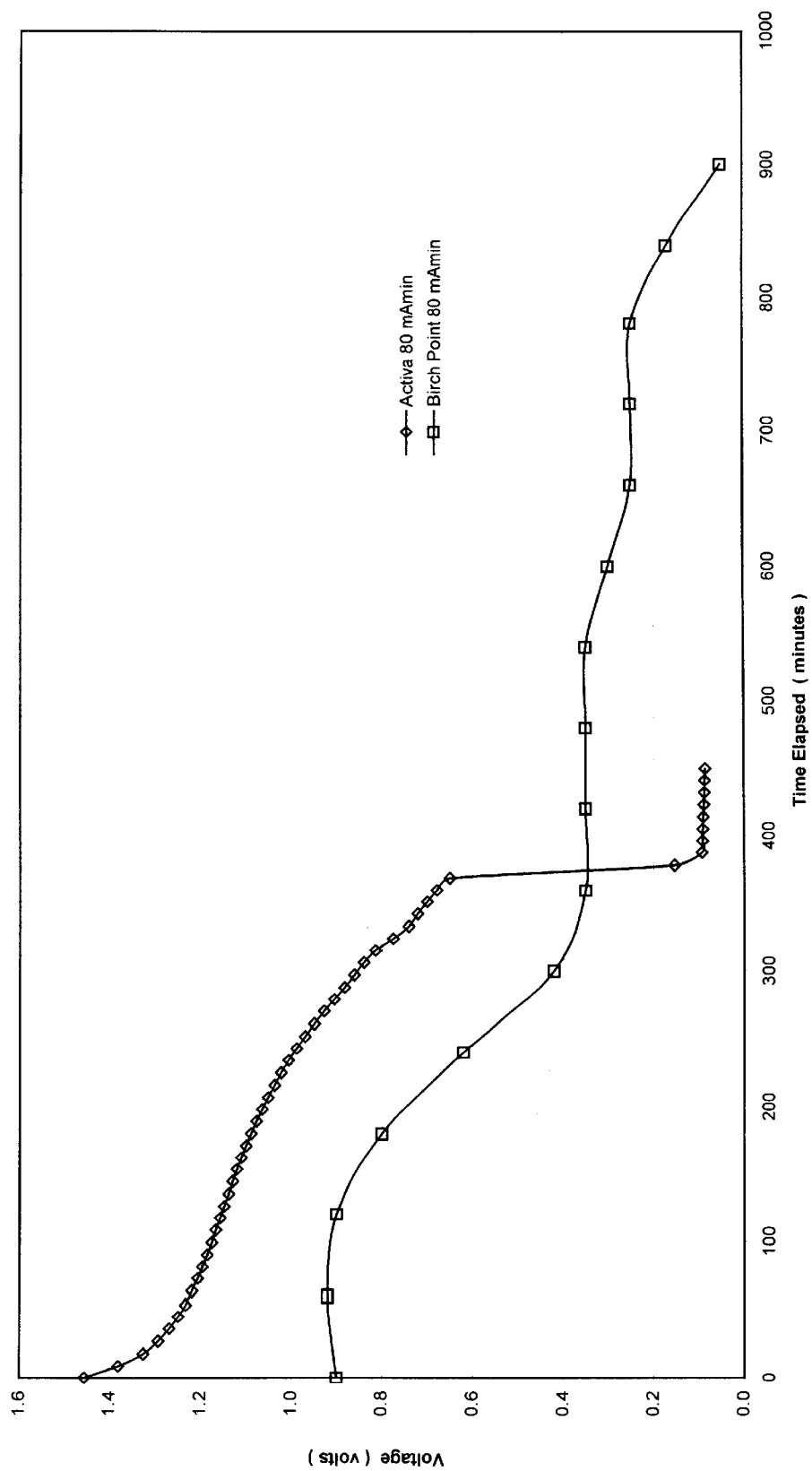
FIG. 13 is a plot of voltage between cationic and anionic chambers during the test illustrated in FIG. 12.

The dispensed ion dose will directly correspond to the current flow through the ion-conducting path. FIGS. 12 and 13 illustrate the performance of a device constructed according to the instant invention compared to a comparable device constructed according to the teachings of the Birch Point application. The Birch Point device was made by forming electrodes from Zn and AgCl. The invention was embodied with a single 1.5 volt button battery rated at 900 mAmp-min. Skin resistance $R_s$ was modeled with a 5 k-ohm resistor. The shunt resistor $R_p$ was 500 ohms. Useful shunt resistances may range from 1 ohm to about 10,000 ohms, or more.

With reference to FIG. 12, it may be seen that the invention delivered a current corresponding to an equivalent dose of beneficial agent totaling about 78 mAmp-min in about 400 minutes. The Birch Point device required over 850 minutes, or more than twice as long, to accomplish the same dose.

FIG. 13 illustrates the voltage measured between the cationic and anionic chambers during the test illustrated in FIG. 12. It may be noted, with reference to FIG. 13, that the trace of voltage over time for the invention is not a perfectly "square" square-wave shape. That is, the voltage drops over time, instead of remaining relatively constant for about the first 375 minutes. The current discharge through both the shunt and skin paths exceeds the battery's steady state discharge rate at which battery voltage may remain relatively constant. However, the voltage does exhibit a sharp drop as the battery approaches full discharge. The battery inherently expends its energy more rapidly and uniformly than the electrolytic cell, and does so up to substantially complete exhaustion. Such a characteristic is desirable as one way to accurately control a treatment dose. The device according to the invention provides a disposable iontophoretic apparatus which is faster in delivering a treatment dose and also more precise in termination of the treatment interval.

Figure 14:
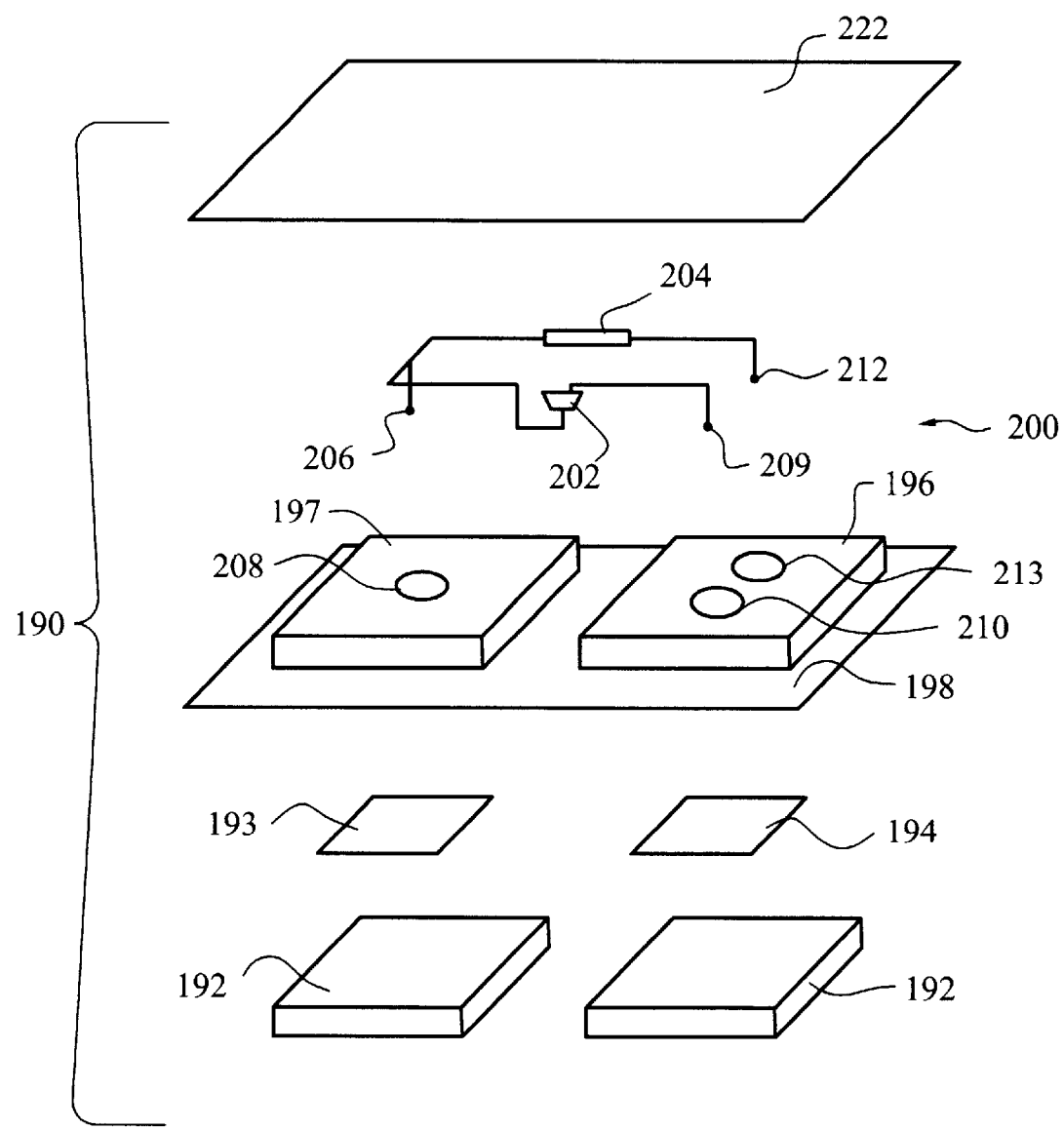
FIG. 14 is an exploded view in perspective of another embodiment of the invention.

One way to manufacture a device to include a shunt resistance in a parallel path between the cationic and anionic chambers is illustrated generally at 190 in FIG. 14. Substrates 192 and electrodes 193, 194 are housed in chambers 196 and 197. Chambers 196 and 197 are formed in container 198, which may beneficially have an adhesive coating on one surface thereof. Circuit elements, generally indicated at 200, are placed on top of container 198. Circuit elements can include a battery 202 and a resistor 204. The battery 202 and resistor 204 are connected at junction 206 through aperture 208 to electrode 193. Battery 202 is connected at junction 209 to electrode 194 through aperture 210 in chamber 196. Resistor 204 has terminal 212 disposed through port 213 in chamber 196, but away from contact with electrode 194. An electrical circuit is formed between junction 209 and terminal 212 only after introduction of an electrolyte to chamber 196. The electrolyte effectively acts as a switch in-circuit with the battery 202 and resistor 204. A protective top cover 222 desirably is placed over the components 200 to provide a pleasing appearance.

While the invention has been described in particular with reference to certain illustrated embodiments, such is not intended to limit the scope of the invention. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An A disposable iontophoretic fluid delivery device comprising:
    a cationic chamber defining a volume in which to hold a cationic substance, a wall of said chamber having a first passageway permitting migration therethrough by ions;
    an anionic chamber defining a volume in which to hold an anionic substance, a wall of said anionic chamber having a second passageway permitting migration therethrough by ions, said first and second passageways being oriented and arranged on a surface of a container to enable creation of an ion conducting path, through a cooperating body, of an electrical circuit between said cationic and anionic chambers;
    a first electromotive cell comprising a mini battery configured to produce a single, approximately square-wave current discharge over the first electromotive cell's working life and comprising first and second poles of opposite electrical sign, said first electromotive cell being disposed in an electron conducting path configured to complete said electrical circuit; and
    a shunt resistance disposed in parallel with an ion conducting path between said cationic and anionic chambers, said shunt resistance selected to control the delivery of fluid from the iontophoretic fluid delivery device;
    wherein a quantity of energy from said mini battery is substantially exhausted after delivery of a treatment dose.

2. The disposable iontophoretic fluid delivery device of claim 1, wherein said first electromotive cell comprising the mini battery is constructed to operate with a metal-anode based electro-chemical reaction, wherein said metal is selected from the group consisting of lithium, zinc, magnesium, and aluminum.

3. The disposable iontophoretic fluid delivery device of claim 1, wherein said container comprises an adhesive patch.

4. The disposable iontophoretic device of claim 3, a value of said shunt resistance being selected to determine a quantity of energy from said mini battery for direction through said ion conducting path for delivery of a beneficial agent.

5. The disposable iontophoretic device of claim 4, wherein said shunt resistance has a value between about 1 Ohm and about 10,000 Ohms.

* * * * *